United States Patent [19]

Nesler

[11] 4,435,852
[45] Mar. 13, 1984

[54] GOGGLE

[76] Inventor: Todd G. Nesler, 2480 Doris, Brighton, Mich. 48116

[21] Appl. No.: 444,321

[22] Filed: Nov. 24, 1982

[51] Int. Cl.³ .............................................. A61F 9/02
[52] U.S. Cl. ...................................................... 2/436
[58] Field of Search .................. 2/436, 437, 439, 447, 2/454

[56] References Cited

U.S. PATENT DOCUMENTS

| 1,805,633 | 5/1931 | Moran et al. | 2/437 |
| 1,916,630 | 7/1933 | Moran et al. | 2/436 X |
| 3,691,565 | 9/1972 | Galonek | 2/436 X |
| 3,838,466 | 10/1974 | Poirier | 2/436 X |
| 4,176,410 | 12/1979 | Matthias | 2/436 |

FOREIGN PATENT DOCUMENTS

| 150848 | 9/1981 | Fed. Rep. of Germany | 2/436 |
| 474999 | 8/1969 | Switzerland | 2/436 |

Primary Examiner—Peter P. Nerbun
Attorney, Agent, or Firm—Gifford, VanOphem, Sheridan, Sprinkle & Nabozny

[57] ABSTRACT

A unique goggle is disclosed with improved ventilation means. The goggle includes a frame having a transparent lens across its forward side and the frame is secured to the head of the user by a strap or the like. In doing so, a goggle chamber is formed between the frame, lens and the head of the user. At least one ventilation port is formed through the frame which is open to the chamber while an elongated ventilation channel is secured to and extends rearwardly from the frame. One end of the channel is open to the goggle chamber while the other end of the channel is open rearwardly of the goggle frame. In use, air is evacuated from the goggle chamber and out through the ventilation channel by venturi forces.

5 Claims, 4 Drawing Figures

U.S. Patent  Mar. 13, 1984  4,435,852 ant# GOGGLE

BACKGROUND OF THE INVENTION

1. Field of the Invention

The present invention relates generally to goggles and, more particularly, to a goggle with improved ventilation means.

2. Description of the Prior Art

Goggles are used in a number of different sports, such as motorcycling, skiing and the like. The previously known goggles typically include a frame having a lens secured across the front side of the frame. The frame is then attached to the head of the user so that the rear side of the frame abuts against the face of the user and around the user's eyes. In doing so, a goggle chamber is formed between the frame, lens and the user's face.

One disadvantage of the previously known goggles is that such goggles are prone to fogging of the lens which, in turn, obscures the vision of the user.

In order to minimize fogging of the goggle lens, a number of previously known goggles include ventilation ports through the goggle frame. These previously known ventilation ports, however, provide only minimal air circulation within the goggle chamber and do not adequately prevent fogging of the lens.

SUMMARY OF THE PRESENT INVENTION

The present invention provides a goggle which overcomes the above mentioned disadvantages of the previously known goggles.

In brief, the goggle of the present invention comprises a frame having a front side and a rear side. A transparent lens is secured across the front side of the frame in any conventional fashion. The frame with its attached lens is then secured to the head and around the eyes of the user by a strap or other conventional means. In doing so, a goggle chamber is formed between the frame, lens and the face of the user.

At least one ventilation port is formed through the frame and open to the goggle chamber. In addition, at least one elongated ventilation channel is secured to and extends rearwardly from the frame. The channel is open at each end so that one end of the channel is open to the goggle chamber while the other chamber is open exteriorly of and spaced rearwardly from the goggle chamber.

In operation, when the user moves in a forward direction the venturi faces on the rear open end of the ventilation channel effectively evacuate air and accumulated moisture from the goggle chamber. The ventilation channel thus effectively eliminates all fogging of the lens during use of the goggles.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which.

DETAILED DESCRIPTION OF PREFERRED EMBODIMENTS OF THE PRESENT INVENTION

Figure 1:
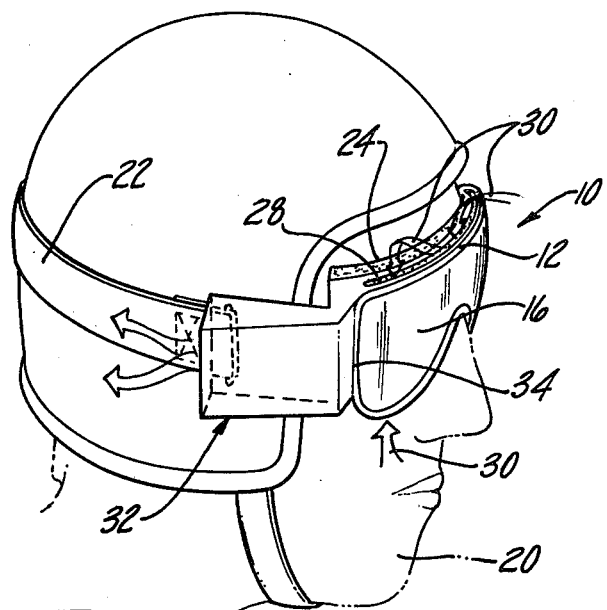
FIG. 1 is a perspective view illustrating a preferred embodiment of the invention.
Figure 2:
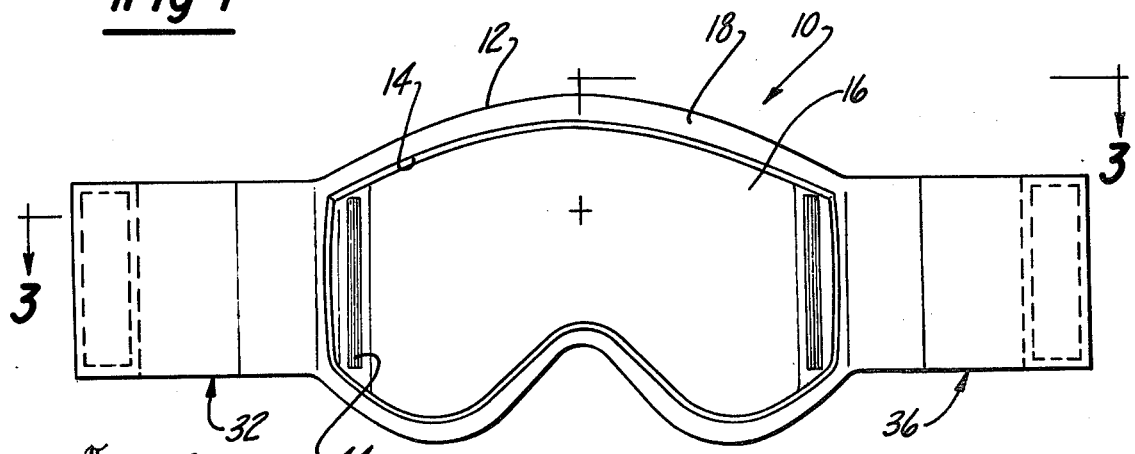
FIG. 2 is a front view of the preferred embodiment of the invention.

With reference first to FIGS. 1 and 2, a preferred embodiment of the goggle 10 of the present invention is thereshown and comprises a frame 12 having an opening 14 formed on its front side 18. A transparent lens 16 is then secured across the front side 18 of the frame 12 and within the opening 14.

Figure 3:
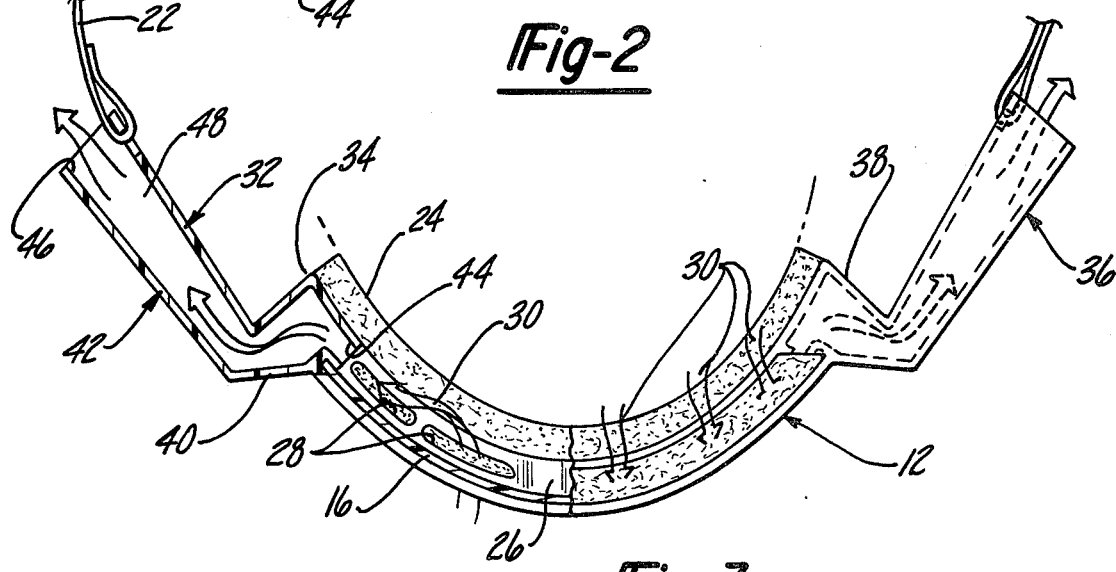
FIG. 3 is a sectional view taken substantially along line 3—3 in FIG. 2.

As best shown in FIGS. 1 and 3, the goggle 10 is secured to the head 20 of a user by a strap 22 or other conventional means. In doing so, a rear side 24 of the frame abuts against the face of the user. Furthermore, the frame 12 is laterally elongated and dimensioned to fit around the eyes of the user thus forming a goggle chamber 26 (FIG. 3) between the frame 12, lens 16 and the face of the user.

Still referring to FIGS. 1 and 3, the frame 12 includes one or more ventilation ports 28 which allows air to flow from outside the goggle 10 and into the goggle chamber 26 as illustrated by arrows 30. The ventilation ports 28, however, are conventional in construction and other types of ventilation ports can be employed without deviation from the spirit or scope of the invention.

Still referring to FIGS. 1 and 3, at least one elongated ventilation channel 32 is secured to one side 34 of the frame 12. Preferably, a second elongated ventilation channel 36 is secured to the other side 38 of the frame 12. Since the ventilation channels 32 and 36 are substantially identical to each other, only the ventilation channel 32 will be described in detail, it being understood that a like desccription shall also apply to the ventilation channel 36.

The ventilation channel 32 includes a first portion 40 which extends laterally outwardly from the frame 12 and a second portion 42 which extends rearwardly from the first portion 40. The channel 32 is tubular and has one end 44 open to the goggle chamber 26. The other end 46 is open at a point spaced rearwardly from and facing rearwardly from the goggle frame 12. Thus, the ventilation channel 32 forms an elongated passageway 48 open to the goggle chamber 26 and this passageway 48 preferably increases in cross sectional area from the front end 44 and toward the rear end 46 of the passageway 48. In addition, although the channel passageway 48 illustrated in the drawing is generally rectangular in cross sectional shape, other shapes can be employed without deviation from the spirit of the invention.

In addition, since the strap 22 is effectively connected to the outer free ends of the first portions 40, the portions 40 function as levers and ensures that the side 24 of the goggle flatly seats against the user's face even through a helmet is worn by the user.

Figure 4:
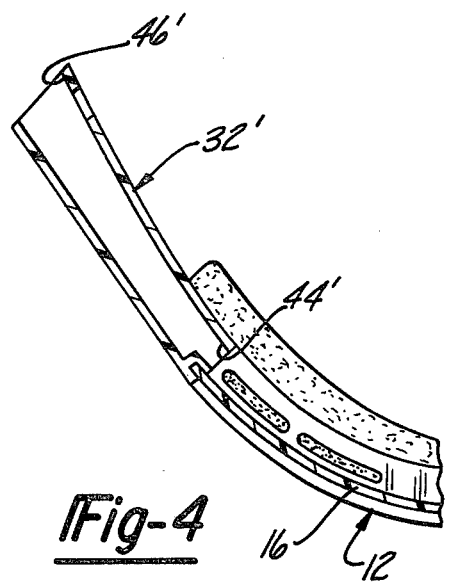
FIG. 4 is a fragmentary sectional view illustrating a second preferred embodiment of the invention.

With reference now to FIG. 4, a second preferred embodiment of the invention is thereshown in which the ventilation channel 32' has one end 44' open to the goggle chamber 26 and its other end 46' open exteriorly of the goggle chamber 26 at a position spaced rearwardly from the frame 12 and thus from the goggle chamber 26. The ventilation channel 32' differs from the ventilation channel 32 shown in FIG. 3 in that the channel 32' is substantially straight and extends rearwardly from the frame 12.

In operation, the goggle 10 is positioned on the head 20 of the wearer as shown in FIG. 1. Then, whenever the wearer of the goggle 10 moves in a forward direction, a venturi force is created across the rear ends 46 of the ventilation channels 32. This venturi force effectively evacuates air out through the passageway 48 in the ventilation channel 32 while fresh air simultaneously enters the goggle chamber 26 through the frame ports 28. In practice, the air flow through the goggle chamber 26 and out through the passages 48 is sufficiently large to prevent all fogging of the goggle lens 16.

Having described my invention, however, many modifications thereto will become apparent to those skilled in the art to which it pertains without deviation from the spirit of the invention as defined by the scope of the appended claims.

I claim:
1. A goggle comprising:
a frame having a front side and a rear side,
a transparent lens secured across the first side of said frame,
means for detachably securing said frame to a head of a user so that said rear side of said frame abuts against the head of the user and thus forming a chamber between said frame, lens and the head of the user,
at least one ventilation port formed through said frame and open to said chamber,
at least one elongated ventilation channel, said channel open at each end and only each such end and defining a fluid passageway between its ends, said channel secured to and extending rearwardly from said frame,
wherein one end of said channel is open to said chamber and,
wherein the other end of said channel faces rearwardly from the rear side of said frame and is open at a position spaced rearwardly from the rear side of said frame.

2. The invention as defined in claim 1 wherein said chamber is laterally elongated and wherein said one end of said channel is open to one side of said chamber.

3. The invention as defined in claim 2 and comprising a second ventilation channel secured to and extending rearwardly from said frame, said second channel having one end open to the other side of said chamber.

4. The invention as defined in claim 2 wherein said channel comprises a first portion extending laterally outwardly from said one side of said chamber and a second portion extending rearwardly from said first portion.

5. The invention as defined in claim 1 wherein the cross sectional area of said fluid passageway increases from said one end of said channel and toward the other end of said channel.

* * * * *

UNITED STATES PATENT AND TRADEMARK OFFICE
CERTIFICATE OF CORRECTION

PATENT NO. : 4,435,852

DATED : March 13, 1984

INVENTOR(S) : TODD G. NESLER

It is certified that error appears in the above—identified patent and that said Letters Patent is hereby corrected as shown below:

Column 2, line 35 delete "desccription" insert --description--.

Column 2, line 56 delete "through" insert --though--.

Signed and Sealed this

Eighteenth Day of December 1984

[SEAL]

Attest:

Attesting Officer

GERALD J. MOSSINGHOFF

Commissioner of Patents and Trademarks